United States Patent
Abe

(10) Patent No.: US 10,172,357 B2
(45) Date of Patent: Jan. 8, 2019

(54) FUNGICIDAL COMPOSITION AND METHOD FOR CONTROLLING PLANT DISEASES

(71) Applicant: ISHIHARA SANGYO KAISHA, LTD., Osaka (JP)

(72) Inventor: Yuzuka Abe, Osaka (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 15/571,406

(22) PCT Filed: May 25, 2016

(86) PCT No.: PCT/JP2016/065502
§ 371 (c)(1),
(2) Date: Nov. 2, 2017

(87) PCT Pub. No.: WO2016/194741
PCT Pub. Date: Aug. 12, 2016

(65) Prior Publication Data
US 2018/0125069 A1   May 10, 2018

(30) Foreign Application Priority Data

May 29, 2015 (JP) .................................. 2015-109896

(51) Int. Cl.
*A01N 43/40* (2006.01)
*A01N 47/34* (2006.01)
*A01C 1/08* (2006.01)

(52) U.S. Cl.
CPC ................ *A01N 43/40* (2013.01); *A01C 1/08* (2013.01); *A01N 47/34* (2013.01)

(58) Field of Classification Search
None
See application file for complete search history.

(56) References Cited

U.S. PATENT DOCUMENTS

| | | |
|---|---|---|
| 2006/0194849 A1 | 8/2006 | Nishide et al. |
| 2011/0104307 A1 | 5/2011 | Ogawa et al. |

FOREIGN PATENT DOCUMENTS

| | | | |
|---|---|---|---|
| CN | 102119698 | | 7/2011 |
| CN | 102119698 A | * | 7/2011 |
| CN | 103120170 | | 5/2013 |
| CN | 103181390 A | * | 7/2013 |
| CN | 104222121 | | 12/2014 |
| EP | 1 679 003 | | 7/2006 |
| JP | 02-174706 | | 7/1990 |
| WO | 02/067679 | | 9/2002 |
| WO | 2005/041663 | | 5/2005 |
| WO | 2008/148178 | | 12/2008 |
| WO | 2010/002026 | | 1/2010 |
| WO | 2014/029697 | | 2/2014 |

OTHER PUBLICATIONS

Macbean, The Pesticide Manual, 2012, British Corp Protection Council, 16th Edition, pp. 504-505, 990-993, 1118-1121.
FRAC Code List (C) 2016: Fungicides sorted by mode of action (including FRAC Code numbering), "www.frac.info/docs/default-source/publications/frac-code-list/frac-code-list-2016.pdf?sfvrsn=2", FRAC Fungicide Resistance Action Committee, 2016, pp. 1-10.
International Search Report issued from Patent Application No. PCT/JP2016/065502, dated Jul. 12, 2016 with English translation.
International Preliminary Report on Patentability from Patent Application No. PCT/JP2016/065502, dated Jul. 12, 2016 with English translation.
Anonymous—Fluazinam Compositions, Research Disclosure, Kenneth Mason Publications, Hamsphire, UK, GB, vol. 438, No. 47, Oct. 1, 2000.
European Search Report issued with respect to Application No. 16803176.3, dated Oct. 25, 2018.

* cited by examiner

*Primary Examiner* — Alton N Pryor
(74) *Attorney, Agent, or Firm* — Greenblum & Bernstein, P.L.C.

(57) ABSTRACT

To provide a fungicidal composition having stable and high controlling effects against plant diseases, particularly preventive and/or curative effects against plant diseases, and a method for controlling plant diseases.
A fungicidal composition comprising, as active ingredients, pyriofenone, (b) fluazinam and (c) thiophanate-methyl, and a method for controlling plant diseases, which comprises applying the fungicidal composition comprising the above active ingredients to plants and/or to a soil in which they grow.

19 Claims, No Drawings

FUNGICIDAL COMPOSITION AND METHOD FOR CONTROLLING PLANT DISEASES

TECHNICAL FIELD

The present invention relates to a fungicidal composition having plant diseases controlling effects, particularly preventive and/or curative effects against plant diseases remarkably improved, a method for controlling plant diseases by using the composition, and a seed coated with the composition.

BACKGROUND ART

Patent Document 1 discloses that a fungicidal composition having excellent fungicidal effects can be obtained by using a benzoylpyridine derivative including 3-(2,3,4-trimethoxy-6-methylbenzoyl)-5-chloro-2-methoxy-4-methylpyridine (pyriofenone) which is an active ingredient of the present invention, and at least one fungicide selected from the group consisting of thiophanate-methyl, carbendazim, polyoxins, fluazinam, quinomethionate, maneb, zineb, mancozeb, polycarbamate, metiram, propineb, cymoxanil, metalaxyl and the like, in combination.

However, it failed to disclose use of three specific active ingredients pyriofenone, fluazinam and thiophanate-methyl as fungicides in combination.

Patent Document 2 discloses that an agricultural fungicidal composition comprising, as active ingredients, N-(3-chloro-5-trifluoromethyl-2-pyridyl)-2,6-dinitro-3-chloro-4-trifluoromethylaniline (fluazinam) and 1,2-di-(3-methoxycarbonyl-2-thioureido)benzene (thiophanate-methyl) which are active ingredients of the present invention, has excellent fungicidal effects as compared with a case where the respective active ingredients are applied individually.

However, it failed to disclose use of the composition in combination with a benzoylpyridine derivative.

Patent Document 3 discloses that use of a fungicidal composition comprising fluazinam which is an active ingredient of the present invention and thiophanate-methyl or carbendazim, in combination with a natural polymer for seed treatment, brings about fungicidal effects against various seed borne diseases.

However, it failed to disclose use of the composition in combination with another fungicide.

PRIOR ART DOCUMENTS

Patent Documents

Patent Document 1: WO2005/041663
Patent Document 2: JP-A-H02-174706
Patent Document 3: WO2008/148178

DISCLOSURE OF INVENTION

Technical Problem

When pyriofenone, fluazinam and thiophanate-methyl which are active ingredients of the present invention (hereinafter sometimes referred to as simply as active ingredients of the present invention) are applied individually, their effects may be insufficient against specific plant diseases, their residual activity will last only for a relatively short period of time, or thiophanate-methyl-resistant fungal pathogen may appear, and they sometimes have practically no sufficient controlling effects against plant diseases.

The object of the present invention is to remarkably improve controlling effects against plant diseases by using the active ingredients of the present invention in combination.

Solution to Problem

The present inventor has conducted extensive studies to achieve the above object and as a result, found that by combining pyrofenone, fluazinam and thiophanate-methyl, excellent fungicidal effects can be obtained, which are unexpected from a case where the active ingredients of the present invention are used individually or in combination of two of them, and accomplished the present invention.

That is, the present invention provides a fungicidal composition comprising, as active ingredients, pyriofenone, fluazinam and thiophanate-methyl, a method for controlling plant diseases, which comprises applying the composition to plants and/or to a soil in which they grow, and a seed coated with the composition.

Advantageous Effects of Invention

The combination of the active ingredients in the fungicidal composition of the present invention (hereinafter sometimes referred to as the composition of the present invention) has stable and high controlling effects against plant diseases, particularly preventive and/or curative effects against plant diseases, and thus the present invention is useful for controlling plant diseases.

DESCRIPTION OF EMBODIMENTS

The active ingredient (a) pyriofenone in the composition of the present invention is a compound of which the structure and the properties are disclosed in The Pesticide Manual (16th edition, British Crop Protection Council), pages 991 to 992.

The active ingredient (b) fluazinam in the composition of the present invention is a compound of which the structure and the properties are disclosed in The Pesticide Manual (16th edition, British Crop Protection Council), pages 504 to 505.

The active ingredient (c) thiophanate-methyl in the composition of the present invention is a compound of which the structure and the properties are disclosed in The Pesticide Manual (16th edition, British Crop Protection Council), pages 1,118 to 1,120.

Each active ingredient of the present invention may be a salt. The salt may be any agriculturally acceptable salt and may, for example, be an alkali metal salt such as a sodium salt or a potassium salt; an alkaline earth metal salt such as a magnesium salt or a calcium salt; an ammonium salt such as a monomethylammonium salt, a dimethylammonium salt or a triethylammonium salt; an inorganic acid salt such as a hydrochloride, a perchlorate, a sulfate or a nitrate; or an organic acid salt such as an acetate, a fumarate or a methanesulfonate.

The composition of the present invention is effective for controlling various plant disease, for example, diseases of Gramineae crops, such as rice diseases such as blast caused by *Magnaporthe grisea*, brown spot caused by *Cochliobolus miyabeanus*, and sheath blight caused by *Rhizoctonia solani*; wheat and barley diseases such as wheat and barley powdery mildew caused by *Erysiphe graminis*, *Fusarium* blight caused by *Fusarium* spp., rust caused by *Puccinia* spp., browning root rot caused by *Pythium* spp., loose smut caused by *Ustilago nuda*, eye spot caused by *Pseudocercosporella herpotrichoides*, and speckled leaf blotch or glume blotch caused by *Septoria* spp.; corn diseases such as leaf spot caused by *Phaeosphaeria* spp., rust caused by *Puccinia* spp., northern leaf blight caused by *Setosphaeria* spp., southern leaf blight caused by *Cochliobolus heterostrophus*, root rot caused by *Pythium grarninicola*, and smut caused by *Ustilago maydis*; and sugar cane diseases such as smut caused by *Ustilago scitaminea*, leaf scorch caused by *Stagonospora* spp., rust caused by *Puccinia* spp., top rot caused by *Gibberella* spp., sooty mold caused by *Caldariomyces* spp., and leaf blight caused by *Pseudocercospora* spp.;

diseases of Legminosae crops, such as powdery mildew caused by *Oidium* spp., rust caused by *Phakopsora* spp., downy mildew caused by *Peronospora* spp., *Phytophthora* rot caused by *Phytophthora* spp., anthracnose caused by *Colletotrichum* spp., sclerotinia rot caused by *Sclerotinia* spp., and gray mold caused by *Botrytis* spp.; diseases of Brassicaceae crops, such as downy mildew caused by *Peronospora* spp., and *Altemaria* leaf spot caused by *Altemaria* spp.;

diseases of Asteraceae crops, such as downy mildew caused by *Bremia* spp., blight caused by *Phytophthora* spp., gray mold caused by *Botrytis* spp., stem rot caused by *Sclerotinia* spp., and rust caused by *Aecidium*;

diseases of Solanaceae crops, such as tomato diseases such as early blight caused by *Altemaria solani*, leaf mold caused by *Fulvia fulva*, late blight caused by *Phytophthora infestans*, gray mold caused by *Botrytis cinerea*, and powdery mildew caused by *Oidiopsis sicula*; and potato diseases such as early blight caused by *Altemaria solani*, late blight caused by *Phytophthora infestans*, and Sclerotial rot caused by *Sclerotinia sclerotiorum*;

diseases of Cucurbitaceae crops, such as anthracnose caused by *Colletotrichum lagenarium*, powdery mildew caused by *Sphaerotheca* spp., gummy stem blight caused by *Didymella bryoniae*, downy mildew caused by *Pseudoperonospora cubensis*, phytophthora rot caused by *Phytophthora* spp., and *Corynespora* leaf spot caused by *Corynespora cassiicola*;

diseases of Allioideae crops, such as downy mildew caused by *Peronospora* spp., *Phytophthora* rot caused by *Phytophthora nicotianae*, gray mold caused by *Botrytis cineraa*, neck rot caused by *Sclerotinia* spp., and rust caused by *Puccinia* spp.;

diseases of Umbelliferae crops, such as leaf blight or *Altemaria* black rot caused by *Altemaria* spp., gray mold caused by *Botyrtis cinerea*, *Sclerotinia* rot caused by *Sclerotinia* spp., powdery mildew caused by *Erysiphe heraclei*, and leaf spot caused by *Cercospora* spp.;

diseases of Liliaceae crops, such as *Botrytis* blight caused by *Botrytis* spp., blight caused by *Phytophthora* spp., and leaf blight caused by *Phomopsis* spp.;

diseases of Polygonaceae crops, such as downy mildew caused by *Peronospora* spp., powdery mildew caused by *Erysiphe polygoni* and damping-off caused by *Rhizoctonia solani*;

diseases of Convolvulaceae crops, such as wilt caused by *Fusarium oxysporum*, black rot caused by *Ceratocystis fimbriata*, and soil rot caused by *Streptomyces ipomoeae*;

diseases of Chenopodiaceae crops, such as downy mildew caused by *Peronospora* spp., *Phytophthora* rot caused by *Phytophthora* spp., gray mold caused by *Botrytis cinerea*, root rot caused by *Sclerotinia sclerotiorum*, powdery mildew caused by *Oidium* spp., and *Cercospora* leaf spot caused by *Cercospora beticola*;

diseases of Vitaceae crops, such as bird's eye rot caused by *Elsinoë ampelina*, ripe rot caused by *Colletotrichum* spp., powdery mildew caused by *Erysiphe necator*, downy mildew caused by *Plasmopara viticola*, gray mold caused by *Botrytis cinerea*, *Cercospora* leaf spot caused by *Pseudocercospora* spp., and swelling arm caused by *Diaporthe kyushuensis*;

diseases of Rosaceae crops, such as strawberry diseases such as powdery mildew caused by *Sphaerotheca aphanis*, gray mold caused by *Botrytis cinera*, and crown rot caused by *Glomerella cingulata*; apple diseases such as *Monilia* leaf blight caused by *Monilinia mali*, powdery mildew caused by *Podosphaera leucotricha*, *Altemaria* leaf spot caused by *Altemaria mall*, scab caused by *Venturia inaequalis*, bitter rot caused by *Glomerella cingulata*, blotch caused by *Diplocarpon mali*, ring rot caused by *Botryosphaeria kuwatsukai*, fly speck caused by *Zygohiala jamaicensis*, sooty blotch caused by *Gloeodes pomigena*, and fruit spot caused by *Mycosphaerella pomi*; Asian pear diseases such as scab caused by *Venturia* spp., black spot caused by *Alternaria* spp., powdery mildew caused by *Phyllactinia* spp., and *Phytophthora* crown and root rot caused by *Phytophthora cactorum*; and peach diseases such as brown rot caused by *Monilinia fructicola*, scab caused by *Cladosphorium carpophilum*, and *Phomopsis* rot caused by *Phomopsis* spp.;

diseases of Rutaceae crops, such as melanoses caused by *Diaporthe citri*, and spot anthracnose caused by *Elsinoë fawcettii*;

diseases of Ebenaceae crops, such as anthracnose caused by *Colletotrichum gloeosporioides*, angular leaf spot caused by *Cercospora kaki*, powdery mildew caused by *Phyllactinia kakicola*, and fly speck caused by *Zygophiala jamaicensis*; and diseases of Theaceae crops, such as Anthracnose caused by *Colletotrichum* spp., gray blight caused by *Pestalotiopsis longiseta*, bacterial shoot blight caused by *Pseudomonas syringae*, and leaf and stem gall caused by *Exobasidium camelliae*.

The composition of the present invention is effective also for controlling various seed borne disease, for example, diseases of Gramineae crops, such as wheat diseases such as *Fusarium* blight caused by *Fusarium* spp., anthracnose caused by *Colletotrichum graminicola*, stinking smut caused by *Tilletia* spp., loose smut caused by *Ustilago* spp., *Cephalosporium* stripe caused by *Cephalosporium gramineum*, and glume blotch caused by *Septoria nodorum*; corn diseases such as southern leaf blight caused by *Bipolaris maydis*, anthracnose caused by *Colletotrichum graminicola*, and seedling blight caused by *Fusarium avenaceum*; and sugar cane diseases such as red rot caused by *Glomerella tucumanensis*, pineapple disease caused by *Ceratocystis paradoxa*, and downy mildew caused by *Sclerospora sacchari*;

diseases of Leguminosae crops, such as soybean diseases such as purple stain caused by *Cercospora kikuchii*, downy mildew caused by *Peronospora manshurica*, *Fusarium* blight caused by *Fusarium oxysporum*, *Septoria* brown spot caused by *Septoria glycines*, pod and stem blight caused by *Diaporthe phaseolorum*, anthracnose caused by *Colletotrichum truncatum*, and sleeping-blight caused by *Septogloeum sojae*;

diseases of Brassicaceae crops, such as cabbage diseases such as *Alternaria* leaf spot caused by *Alternaria brassicae*, alternaria sooty spot caused by *Alternaria brassicicola*, downy mildew caused by *Peronospora parasitica*, bacterial leaf spot caused by *Pseudomonas cannabina*, black rot caused by *Xanthomonas campestris*, and black leg caused by *Phoma lingam*; Japanese radish diseases such as *alternaria* leaf spot caused by *Alternaria brassicae*, yellows caused by *Fusarium oxysporum*, and black rot caused by *Xanthomonas campestris*; and Chinese cabbage diseases such as *alternaria* leaf spot caused by *Alternaria brassicae*, black rot caused by *Xanthomonas campestris*, and yellows caused by *Verticillium dahliae*;

diseases of Solanaceae crops, such as tomato diseases such as early blight caused by *Alternaria solani*, bacterial canker caused by *Clavibacter michiganensis*, and bacterial spot caused by *Xanthomonas vesicatoria*; eggplant diseases such as early blight caused by *Alternaria solani*, and brown spot caused by *Phomopsis vexans*; and potato diseases such as scab caused by *Streptomyces* spp., silver scurf caused by *Helminthosporium solani*, and powdery scab caused by *Spongospora subterranea*;

diseases of Cucurbitaceae crops, such as cucumber diseases such as leaf blight caused by *Alternaria alternata*, bacterial spot caused by *Pseudomonas syringae*, and bacterial brown spot caused by *Xanthomonas cucurbitae*;

diseases of Allioideae crops, such as onion diseases such as *Alternaria* leaf spot caused by *Alternaria porri*, gray mold neck rot or Mycelial neck rot caused by *Botrytis* spp., *Fusarium* basal rot caused by *Fusarium oxysporum*, and downy mildew caused by *Peronospora destructor*;

diseases of Umbelliferae crops, such as carrot diseases such as leaf blight or *Alternaria* black rot caused by *Alternaria* spp., and bacterial blight caused by *Xanthomonas hortorum*; and celery diseases such as late blight caused by *Septoria apiicola*, stem rot caused by *Sclerotinia sclerotiorum*, and bacterial leaf blight caused by *Pseudomonas syringae*; and diseases of Chenopodiaceae crops, such as spinach diseases such as downy mildew caused by *Peronospora farinosa*, *Fusarium* wilt caused by *Fusarium oxysporum*, and anthracnose caused by *Colletotrichum spinaciae*.

The composition of the present invention is effective also for controlling soil diseases caused by plant disease pathogens such as *Fusarium* spp., *Pythium* spp., *Rhizoctonia* spp., *Verticillium* spp., *Plasmodiophora* spp., and *Thielaviopsis* app.

The plants to be protected from various plant disease pathogens by the composition and the controlling method of the present invention are not particularly limited so long as they are agriculturally useful. They may, for example, be Gramineae crops (such as rice, wheat, barley, oat, rye, corn and sugar cane), Leuminosae crops (such as soybean, kidney bean and adzuki bean), Brassicaceae crops (such as cabbage, Chinese cabbage, Japanese radish, turnip, broccoli, cauliflower and Turnip rape), Asteraceae crops (such as lettuce, burdock and crown daisy), Solanaceae crops (such as potato, eggplant, tomato, sweet pepper and tobacco), Cucurbitaceae crops (such as cucumber, pumpkin, melon and watermelon), Allioideae crops (such as Welsh onion, Chinese chive, *Allium chinense* and garlic), Umbelliferae crops (such as celery, carrot and parsley), Liliaceae crops (such as lily, tulip and asparagus), Polygonaceae crops (such as buckwheat), Convolvulaceae crops (such as sweet potato), Chenopodiaceae crops (such as spinach and sugar beet), Vitaceae crops (such as grape), Rosaceae crops (such as rose, strawberry, apple, Asian pear, pear, peach, loquat and almond), Rutaceae crops (such as mandarin orange, lemon and orange), Ebenaceae crops (such as Japanese persimmon) and Theaceae crops (such as tea).

So long as the purpose of the present invention can be accomplished, the composition of the present invention may be used as it is or, in the same manner as conventional agricultural chemicals, may be mixed with various adjuvants and formulated into various formulations commonly used in this field such as a dust, granules, water dispersible granules, a wettable powder, a water-based suspension concentrate, an oil-based suspension concentrate, water soluble granules, an emulsifiable concentrate, a soluble concentrate, a paste, an aerosol and an ultra low-volume formulation.

When such a formulation is prepared, the active ingredients of the present invention may be mixed and formulated together, or may be individually formulated.

Such adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethyl sulfoxide, dimethylformamide, dimethylacetamide, N-methyl-2-pyrrolidone and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an acyl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Such adjuvants may be selected from those known in this field so long as the purpose of the present invention can thereby be accomplished. Further, various additives which are commonly used, such as a filler, a thickener, an anti-settling agent, an anti-freezing agent, a dispersion stabilizer, a phytotoxicity reducing agent, and an anti-mold agent, may also be employed. The blend ratio of the active ingredients of the present invention to the various adjuvants (active ingredients: adjuvants) is usually from 0.005:99.995 to 95:5, preferably from 0.2:99.8 to 90:10 by the mixing weight ratio. In the actual application of such a formulation, it may be used as it is, or may be diluted to a predetermined concentration with a diluent such as water, and various spreaders may be added thereto, as the case requires.

Further, in the present invention, other agricultural chemicals such as a fungicide, an insecticide, a miticide, a nematicide, a soil insect pesticide, an antivirus agent, an attractant, a herbicide and a plant growth regulating agent, may be used in combination, whereby more excellent effects may sometimes be obtained.

The active ingredient compounds of a fungicide in the above-mentioned other agricultural chemicals may properly be selected, for example, from the following group of compounds (by common names or test codes of Japan Plant Protection Association). In a case where these compounds have their salts, alkyl esters, various structural isomers such as optical isomers, etc., all of them are included, of course, even if no specific disclosure thereof is made.

Anilinopyrimidine compounds such as mepanipyrim, pyrimethanil and cyprodinil;

triazolopyrimidine compounds such as 5-chloro-7-(4-methylpiperidin-1-yl)-6-(2,4,6-trifluorophenyl)[1,2,4]triazolo[1,5-a]pyrimidine;

azole compounds such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, prothioconazole, triadimenol, flutriafol, difenoconazole, fluquinconazole, fenbuconazole, bromuconazole, diniconazole, tricyclazole, probenazole, simeconazole, pefurazoate, ipconazole, imibenconazole, azaconazole, triticonazole, imazalil, ipfentrifluconazole and mefentrifluconazole;

quinoxaline compounds such as quinomethionate;

dithiocarbamate compounds such as maneb, zineb, mancozeb, polycarbamate, metiram, propineb and thiram;

organic chlorine compounds such as fthalide, chlorothalonil and quintozene;

imidazole compounds such as benomyl, carbendazim, thiabendazole and fuberiazole;

cyanoacetamide compounds such as cymoxanil;

anilide compounds such as metalaxyl, metalaxyl-M (another name: mefenoxam), oxadixyl, ofurace, benalaxyl, benalaxyl-M (another name: kiralaxyl, chiralaxyl), furalaxyl, cyprofuram, carboxin, oxycarboxin, thifluzamide, boscalid, bixafen, isotianil, tiadinil, sedaxane and pyrazifumid;

sulfamide compounds such as dichlofluanid;

copper compounds such as cupric hydroxide, oxine copper, anhydrous copper sulfate, copper nonylphenolsulfonate, copper 8-hydroxyquinoline and dodecylbenzenesulfonic acid bisethylenediamine copper(II) salt (another name: DBEDC);

organophosphorus compounds such as fosetyl-aluminum, tolclofos-methyl, edifenphos and iprobenfos;

phthalimide compounds such as captan, captafol and folpet;

dicarboxyimide compounds such as procymidone, iprodione and vinclozolin;

benzanilide compounds such as flutolanil, mepronil and benodanil;

amide compounds such as penthiopyrad, penflufen, furametpyr, isopyrazam, silthiopham, fenoxanil, fenfuram, fluxapyroxad, benzovindiflupyr and pydiflumetofen;

benzamide compounds such as fluopyram and zoxamide;

thiophenamide compounds such as isofetamid;

piperazine compounds such as triforine;

pyridine compounds such as pyrifenox and pyrisoxazole;

carbinol compounds such as fenarimol and nuarimol;

piperidine compounds such as fenpropidin;

morpholine compounds such as fenpropimorph and tridemorph;

organotin compounds such as fentin hydroxide and fentin acetate;

urea compounds such as pencycuron;

carboxylic acid amide compounds such as dimethomorph, flumorph, pyrimorph, iprovalicarb, benthiavalicarb-isopropyl, valifenalate and mandipropamid;

phenyl carbamate compounds such as diethofencarb;

cyanopyrrole compounds such as fludioxonil and fenpiclonil;

strobilurin compounds such as azoxystrobin, kresoxim-methyl, metominostrobin, trifloxystrobin, picoxystrobin, oryzastrobin, dimoxystrobin, pyraclostrobin, fluoxastrobin, enestroburin, pyraoxystrobin, pyrametostrobin, coumoxystrobin, enoxastrobin, fenaminstrobin, flufenoxystrobin, triclopyricarb and mandestrobin;

oxazolidinone compounds such as famoxadone;

thiazolecarboxamide compounds such as ethaboxam;

imidazolinone compounds such as fenamidone;

hydroxyanilide compounds such as fenhexamid;

sulfonamide compounds such as flusulfamide, amisulbrom and cyazofamid;

oxime ether compounds such as cyflufenamid;

anthraquinone compounds such as dithianon;

crotonic acid compounds such as meptyldinocap;

antibiotics such as validamycin, kasugamycin and polyoxins;

guanidine compounds such as iminoctadine and dodine;

quinoline compounds such as tebufloquin, quinoxyfen and quinofumelin;

thiazolidine compounds such as flutianil;

carbamate compounds such as propamocarb hydrochloride, pyribencarb, tolpocarb and picarbutrazox;

aryl phenyl ketone compounds such as metrafenone;

sulfur compounds such as sulfur and lime sulfur;

and other compounds such as isoprothiolane, pyroquilon, diclomezine, chloropicrin, dazomet, metam-sodium, nicobifen, diclocymet, proquinazid, fluopicolide, carpropamid, ferimzone, spiroxamine, fenpyrazamine, ametoctradin, oxathiapiprolin, dipymetitrone, SB-4303, BAF-1107, MIF-1002, KUF-1411, BAF-1120, BAF-1510, BAF-1511, NF-180, S-2399, SYJ-264, SYJ-259, AKD-5195, and BYF-1303.

Microbial fungicides include *Bacillus amyloliqefaciens* strain QST713, *Bacillus amyloliqefaciens* strain FZB24, *Bacillus amyloliqefaciens* strain MBI600, *Bacillus amyloliqefaciens* strain D747. *Pseudomonas fluorescens, Bacillus subtilis* and *Trichoderma* atroviride SKT-1.

Plant extracts include tea tree oil.

The active ingredient compounds of insect pest control agents, such as the insecticide, the miticide, the nematicide and the soil insect pesticide in the above-mentioned other agricultural chemicals, may properly be selected, for example, from the following group of compounds (by common names or test codes of Japan Plant Protection Association). In a case where these compounds have their salts, alkyl esters, various structural isomers such as optical isomers, etc., all of them are included, of course, even if no specific disclosure thereof is made.

Organic phosphate compounds, such as profenofos, dichlorvos, fenamiphos, fenitrothion, EPN ((RS)—(O-ethyl O-4-nitrophenyl phenylphosphonothioate), diazinon, chlorpyrifos, chlorpyrifos-methyl, acephate, prothiofos, fosthiazate, cadusafos, disulfoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlorvinphos, chlorfenvinphos, cyanophos, trichlorfon, methidathion, phenthoate, oxydeprofos (another name: ESP), azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet and phorate;

carbamate compounds, such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC (3,5-xylyl methylcarbamate) and fenothiocarb;

nereistoxin derivatives, such as cartap, thiocyclam, thiocyclam oxalate, thiocyclam hydrochloride, bensultap, thiosultap, monosultap (another name: thiosultap-monosodium), bisultap (another name: thiosultap-disodium) and polythialan;

organic metal compounds, such as fenbutatin oxide and cyhexatin;

pyrethroid compounds, such as fenvalerate, permethrin, cypermethrin, alpha-cypermethrin), zeta-cypermethrin, theta-cypermethrin, beta-cypermethrin, deltamethrin, cyhalothrin, gamma-cyhalothrin, lambda-cyhalothrin, tefluthrin, kappa-tefluthrin, ethofenprox, flufenprox, cyfluthrin, beta-cyfluthrin, fenpropathrin, flucythrinate, fluvalinate, cycloprothrin, pyrethrins, esfenvalerate, tetramethrin, resmethrin, protrifenbute, bifenthrin, kappa-bifenthrin, acrinathrin, allethrin, tau-fluvalinate, tralomethrin, profluthrin, metofluthrin, epsilon-metofluthrin, heptafluthrin, phenothrin, flumethrin, momfluorothrin, epsilon-momfluorothrin, silafluofen and chloroprallethrin;

benzoylurea compounds, such as diflubenzuron, chlorfluazuron, teflubenzuron, flufenoxuron, lufenuron, novaluron, triflumuron, hexaflumuron, bistrifluron, noviflumuron and fluazuron;

juvenile hormone-like compounds, such as methoprene, pyriproxyfen, fenoxycarb and diofenolan;

pyridazinone compounds, such as pyridaben;

pyrazole compounds, such as fenpyroximate, fipronil, tebufenpyrad, ethiprole, tolfenpyrad, acetoprole, pyrafluprole, pyriprole, cyenopyrafen, pyflubumide and flufiprole;

neonicotinoid compounds, such as imidacloprid, nitenpyram, acetamiprid, thiacloprid, thiamethoxam, clothianidin, nidinotefuran, dinotefuran and nithiazine;

hydrazine compounds, such as tebufenozide, methoxyfenozide, chromafenozide and halofenozide;

pyridine compounds, such as pyridalyl and flonicamid;

cyclic keto-enol compounds, such as spirodiclofen, spiromesifen and spirotetramat;

strobilurin compounds, such as fluacrypyrim and pyriminostrobin;

pyrimidinamine compounds, such as flufenerim and pyrimidifen;

organic sulfur compounds, such as malathion;

triazine compounds, such as cyromazine;

hydrazone compounds, such as hydramethylnon;

diamide compounds, such as flubendiamide, chlorantraniliprole, cyantraniliprole, cyclaniliprole, tetraniliprole, broflanilide and cyhalodiamide;

thiourea compounds, such as diafenthiuron and chioromethiuron;

formamidine compounds, such as amitraz, chlordimeform and chioromebuform, and other compounds, such as buprofezin, hexythiazox, triazamate, pymetrozine, chlorfenapyr, indoxacarb, acequinocyl, etoxazole, 1,3-dichloropropene, benclothiaz, bifenazate, propargite, clofentezine, metaflumizone, cyflumetofen, pyrifluquinazone, fenazaquin, amidoflumet, sulfluramid, hydramethylnon, metaldehyde, sulfoxaflor, fluensulfone, verbutin, dicloromezotiaz, triflumezopyrim, fluhexafon, tioxazafen, afidopyropen, flometoquin, flupyradifurone, fluazaindolizine and fluxametamide.

Further, it may be mixed with or used in combination with microbial agricultural chemicals, such as insecticidal crystal proteins produced by *Bacillus thuringiensis aizawai*, *Bacillus thuringiensis kurstaki*, *Bacillus thuringiensis israelensis*, *Bacillus thuringiensis japonensis*, *Bacillus thuringiensis tenebrionis* or *Bacillus thuringiensis*, insect viruses, etomopathogenic fungi, and nematophagous fungi:

antibiotics or semisynthetic antibiotics, such as avermectin, emamectin benzoate, milbemectin, milbemycin, spinosad, ivermectin, lepimectin, abamectin, emamectin and spinetoram;

natural products, such as azadirachtin, rotenone, and ryanodine;

repellents, such as deet; and physical controlling agents, such as paraffin oil and mineral oil.

In the present invention, as the application method, a proper method can be employed among various methods depending upon various conditions such as the plants to be treated, the application method, the type of the formulation and the dose, and for example, the following methods may be mentioned.

(1) Pyriofenone, fluazinam and thiophanate-methyl are separately formulated, and the formulations are applied to plants and/or to a soil in which plants grow as they are or as diluted to predetermined concentrations with e.g. water, and as the case requires, as mixed with a spreader (such as a surfactant, a vegetable oil or a mineral oil).

(2-1) Pyriofenone and fluazinam are formulated together, and thiophanate-methyl is formulated, and the formulations are applied to plants and/or to a soil in which plants grow as they are or as diluted to predetermined concentrations with e.g. water, and as the case requires, as mixed with a spreader (such as a surfactant, a vegetable oil or a mineral oil).

(2-2) Pyriofenone and thiophanate-methyl are formulated together, and fluazinam is formulated, and the formulations are applied to plants and/or to a soil n which plants grow as they are or as diluted to predetermined concentrations with e.g. water, and as the case requires, as mixed with a spreader (such as a surfactant, a vegetable oil or a mineral oil).

(2-3) Fluazinam and thiophanate-methyl are formulated together, and pyriofenone is formulated, and the formulations are applied to plants and/or to a soil in which plants grow as they are or as diluted to predetermined concentrations with e.g. water, and as the case requires, as mixed with a spreader (such as a surfactant, a vegetable oil or a mineral oil).

(3) Pyriofenone, fluazinam and thiophanate-methyl are formulated together, and the formulation is applied to plants and/or to a soil in which plants grow as it is or as diluted to a predetermined concentration with e.g. water, and as the case requires, as mixed with a spreader (such as a surfactant, a vegetable oil or a mineral oil).

In the above application methods (1) and (2-1) to (2-3), the respective formulations may be mixed when diluted to predetermined concentrations with e.g. water so that they are applied to plants and/or to a soil in which plants grow simultaneously, or they may be applied continuously or with an appropriate interval. In order to obtain effects of the present invention more effectively, it is preferred to apply pyriofenone, fluazinam and thiophanate-methyl simultaneously.

The formulation of the present invention or a diluted product thereof may be applied by an application method to plants and/or to a soil in which they grow (for example, to plants, seeds, soil, cultivation carriers, etc.) which is commonly used, such as spraying (such as spraying, jetting, misting, atomizing, powder or grain scattering, or dispersing in water), soil application (such as mixing or drenching) or surface application (such as coating, powdering, smearing or covering). Further, it may be applied also by a so-called ultra low-volume application method. In this method, the formulation may be composed of 100% of the active ingredients.

Effects by the seed treatment include, for example, decay prevention, improvement in the germination rate, prevention of infection by soil pathogens, prevention of damping-off, prevention of initial infection after germination, and prevention of onset of diseases at the initial stage of growth, thus leading to a decrease in the density of pathogens and thus prevention of onset of diseases during the entire growing period, by fungicidal/fungistatic activity against pathogens attached to the inside or outside of seeds.

The plants to which the seed treatment is applicable are not particularly limited so long as they are agriculturally useful. The plants include, for example, Gramineae crops (such as rice, wheat, barley, oat, rye, corn and sugar cane), Leguminosae crops (such as soybean, kidney bean and adzuki bean), Brassicaceae crops (such as cabbage, Chinese cabbage, Japanese radish, turnip, broccoli, cauliflower and Turnip rape), Asteraceae crops (such as lettuce, burdock and crown daisy), Solanaceae crops (such as potato, eggplant, tomato, sweet pepper and tobacco), Cucurbitaceae crops (such as cucumber, pumpkin, melon and watermelon), Allioideae crops (such as Welsh onion, chinese chive, *Allium chinense* and garlic), Umbelliferae crops (celery, carrot and parsley), Liliaceae crops (such as lily, tulip and asparagus), Polygonaceae crops (such as buckwheat), Convolvulaceae crops (such as sweet potato) and Chenopodiaceae crops (such as spinach and sugar beet).

The seed treatment may be conducted by any method so long as the composition containing the active ingredients of the present invention is applied to seeds before seeding by an optional method such as a method of attaching the composition to the surface of seeds, or a method of making the composition be absorbed in the seeds.

More specific methods of application to seeds include, for example, dipping, coating, powdering, smearing, film coating and covering granulation, and dipping, smearing, film coating or covering granulation is preferred, and film coating or covering granulation is more preferred.

For film coating, the active ingredients of the present invention are dissolved or dispersed in an aqueous solution of a water-soluble polymer and/or a hydrophilic polymer as the coating agent, and the solution or dispersion is fixed in a film form to the surface of seeds e.g. by spraying and is air-dried or forced-air-dried at a low temperature of 40° C. or below. In order to improve the adhesion of the active ingredients of the present invention and to improve handling efficiency and safety, the coating agent may contain a plasticizer, a binding agent, an inorganic metal compound, a coloring agent, a repellent, etc.

The water-soluble polymer may, for example, be polyethylene glycol, a cellulose derivative, polyvinyl alcohol, polyvinyl pyrolidone, a polyacrylate or its polymer, or a polysaccharide, and the hydrophilic polymer may, for example, be an emulsion of e.g. vinyl acetate or polyurethane, and they may be used alone or as mixed.

The amount of the water-soluble polymer and/or the hydrophilic polymer cannot generally be defined since it varies depending upon the shape, the size and the weight of the seeds, and is usually from 0.1 to 20 wt %, preferably from 0.5 to 10 wt % based on the entire coating agent.

The plasticizer may, for example, be an aliphatic substance such as propylene glycol, polyethylene glycol, polypropylene glycol, glycerine, sorbitol, glycerol triacetate, diethyl phthalate, lauric acid, sucrose, dextrose, sorbitol, triacetin, acetyl triethyl citrate, triethyl citrate, tributyl citrate, acetyl tributyl citrate, a fatty acid, a fatty alcohol, a fatty acid ester or a derivative thereof, or an ester of ethanol or butanol and phthalic acid, citric acid or sebacic acid. Specifically, polyethylene glycol or glycerol is preferred. The amount of the plasticizer used is usually from 0.01 to 10 wt %, preferably from 0.1 to 5 wt % based on the entire coating agent.

The binding agent may, for example, be polyvinyl pyrolidone or a lignosulfonate such as copper lignosulfonate, zinc lignosulfonate, magnesium lignosulfonate, manganese lignosulfonate, sodium lignosulfonate, calcium lignosulfonate or ammonium lignosulfonate, and they may be used alone or in combination. The amount of the binding agent used is usually from 0.001 to 10 wt %, preferably from 0.01 to 1 wt % based on the entire coating agent.

The inorganic metal compound may, for example, be iron or titanium oxide, and is preferably titanium oxide. In order to improve solvophilicity and dispersibility, titanium oxide is preferably one surface-treated with an oxide of e.g. aluminum, silicon, zinc, antimony or zirconium or with an organic substance, and is more preferably one surface-treated with aluminum oxide and/or silicon dioxide. The amount of the inorganic metal compound used cannot generally be defined since it varies depending upon the size, the shape and the weight of seeds, and is usually from 5 to 80 wt %, preferably from 15 to 70 wt % based on the entire coating agent.

The coloring agent may be either a dye or a pigment. The amount of its use cannot be generally defined since it varies depending upon the color tone, and is usually from 0.5 to 30 wt % based on the entire coating agent. Further, a brightener such as mica or polyethylene glycol may be used in combination so as to achieve gloss.

Covering granulation is not particularly limited so long as the seed surface is covered with a powder material. For example, the surface of seeds is covered with a powder material and water and/or a water-soluble binding agent as the coating agent. In such a case, seeds are put in a coating apparatus, the surface of the seeds is coated with water or a binding agent-containing aqueous solution e.g. by spraying while the coating apparatus is rotated, and then the powder material is put and the powder and the seeds are bonded, whereby a covering layer is formed on the surface of the seeds. The thickness of the covering layer may be adjusted by the number of repetition of this operation. The particle size of the coated seeds is usually from about 1 mm to about 5 mm, and the particle size and the covering layer thickness are properly determined depending upon the size, the shape, etc. of bare seeds.

The powder material may, for example, be diatomaceous earth, aluminum hydroxide, barium hydroxide, magnesium hydroxide, calcium sulfate, basic magnesium carbonate, silica, calcium sulfite, calcium carbonate, calcium silicate, illite, halloysite, millicite, vermiculite, peat moss, sand or clay. The amount of the powder material used is usually from 1 to 90 wt %, preferably from 5 to 75 wt % based on the entire coating agent.

The water-soluble binding agent may, for example, be starch, polyvinyl alcohol, carboxymethyl cellulose, methyl cellulose, hydroxypropyl methylcellulose or gelatin. The amount of the water-soluble binding agent used is usually from 0.001 to 10 wt %, preferably from 0.01 to 1 wt % based on the entire coating agent.

The effective amounts of the active ingredients in the composition of the present invention cannot generally be defined since they vary depending upon the conditions such as the plants to be treated, the application method, the type of the formulation, the dose and the application time. In the case of foliar application, the total amount of the active ingredients in the composition of the present invention is usually from 5 to 10,000 g/ha, preferably from 10 to 5,000 g/ha, more preferably from 100 to 2,500 g/ha. In the case of seed treatment, the total amount of the active ingredients in the composition of the present invention is usually from 1 to 2,000 g, preferably from 3 to 700 g, more preferably from 11 to 400 g per 100 kg of the seed weight. In the case of soil application, the total amount of the active ingredients in the present invention is usually from 5 to 10,000 g/ha, preferably from 10 to 5,000 g/ha, more preferably from 100 to 1,000 g/ha.

The effective concentration of the active ingredients contained in the composition of the present invention cannot generally be defined since it varies depending upon the conditions such as the plants to be treated, the application method, the type of the formulation, the dose and the application time. In the case of foliar application or soil treatment, the effective concentrations of pyriofenone, fluazinam and thiophanate-methyl are usually from 0.01 ppm to 100,000 ppm, preferably from 0.1 ppm to 10,000 ppm, more preferably from 1 ppm to 1,000 ppm, respectively. In the case of seed treatment, the effective concentration of pyriofenone is usually from 0.25 to 500 g/100 kg seed, preferably from 10 to 200 g/100 kg seed, the effective concentration of fluazinam is usually from 0.125 to 250 g/100 kg seed, and the effective concentration of thiophanate-methyl is usually from 0.5 to 1,000 g/100 kg seed, preferably from 1 to 400 g/100 kg seed.

The weight ratio of pyriofenone, fluazinam and thiophanate-methyl is not particularly limited and may be adjusted within a relatively wide range depending upon the plants to be treated, the application site and the application method. The weight ratios of optional two ingredients between pyriofenone, fluazinam and thiophanate-methyl, that is, the weight ratios of pyriofenone:fluazinam, fluazinam:thiophanate-methyl and pyriofenone:thiophanate-methyl are each independently from 1:10,000 to 10,000:1, preferably from 1:1,000 to 1,000:1, more preferably from 1:100 to 100:1.

More specifically, in the case of foliar application or soil treatment, based on 1 part by weight of pyriofenone, the amount of fluazinam is usually from 0.0001 to 10,000, preferably from 0.001 to 1,000 parts by weight, more preferably from 0.01 to 100 parts by weight, and the amount of thiophanate-methyl is usually from 0.0001 to 10,000 parts by weight, preferably from 0.001 to 1,000 parts by weight, more preferably from 0.01 to 100 parts by weight. In the case of seed treatment, based on 1 part by weight of pyriofenone, the amount of fluazinam is usually from 0.001 to 10 parts by weight, preferably from 0.01 to 1 part by weight, more preferably from 0.05 to 0.5 part by weight, and the amount of thiophanate-methyl is usually from 0.001 to 10 parts by weight, preferably from 0.1 to 10 parts by weight, more preferably from 0.5 to 5 parts by weight.

Preferred embodiments of the present invention will be described below.

(1) A fungicidal composition comprising, as active ingredients, (a) pyriofenone, (b) fluazinam and (c) thiophanate-methyl.

(2) The fungicidal composition according to (1), wherein the weight ratio of two active ingredients selected from the group consisting of (a) pyriofenone, (b) fluazinam and (c) thiophanate-methyl is from 1:10,000 to 10,000:1.

(3) A method for controlling plant diseases, which comprises applying the fungicidal composition as defined in (1) or (2) to plants and/or to a soil in which they grow.

(4) The method for controlling plant diseases according to (3), wherein the application is conducted by spraying, drenching, seed treatment or dipping.

(5) The method for controlling plant diseases according to (3) or (4), wherein (a) pyriofenone, (b) fluazinam and (c) thiophanate-methyl are applied in a total amount of from 5 to 10,000 g/ha.

(6) The method for controlling plant diseases according to (4), wherein in the seed treatment, (a) pyriofenone, (b) fluazinam and (c) thiophanate-methyl are applied in a total amount of from 1 to 2,000 g/100 kg seed.

(7) The method for controlling plant diseases according to any one of (3) to (6), wherein the plants are Gramineae crops, Leguminosae crops, Brassicaceae crops, Asteraceae crops, Solanaceae crops, Cucurbitaceae crops, Allioideae crops, Umbelliferae crops, Liliaceae crops, Polygonaceae crops, Convolvulaceae crops, Chenopodiaceae crops, Vitaceae crops, Rosaceae crops, Rutaceae crops, Ebenaceae crops, or Theaceae crops.

(8) A seed coated with the fungicidal composition as defined in (1) or (2).

(9) The seed according to (8), which is coated with (a) pyriofenone, (b) fluazinam and (c) thiophanate-methyl in a total amount of from 1 to 2,000 g/100 kg seed.

(10) The seed according to (8) or (9), which is a seed of Gramineae crops, Leguminosae crops, Brassicaceae crops, Asteraceae crops, Solanaceae crops, Cucurbitaceae crops, Allioideae crops, Umbelliferae crops, Liliaceae crops, Polygonaceae crops, Convolvulaceae crops, or Chenopodiaceae crops.

EXAMPLES

Now, the present invention will be described with reference to Test Examples. However, it should be understood that the present invention is by no means restricted thereto.

Test Example 1 (Test on Preventive Effect Against Wheat Powdery Mildew)

50 g of wheat seeds (cultivar: Norin-61-go), and predetermined amounts of an aqueous suspension containing pyriofenone 30% (WN) (tradename: PROPERTY FLOWABLE), an aqueous suspension containing fluazinam 50%

(WN) (tradename: FROWNCIDE SC) and an aqueous suspension containing thiophanate-methyl 75% (WM) (tradename: TOPSIN M sol) so that the respective active ingredient amounts were as identified in Table 1 (g.a.i./100 kg seed), were put in a plastic bag, sufficiently stirred and air-dried to obtain seeds coated with a fungicidal composition. Ten seeds coated with a fungicidal composition were sown in a plastic pot (diameter: 7.5 cm, height: 6.8 cm, cylindrical black plastic pot, soil: culture soil). Wheat plants were cultivated in a greenhouse and at the 1-leaf stage, conidia of *Blumeria graminis* were dusted and inoculated, and the wheat plants were maintained in a constant temperature chamber at 20° C. The test results are shown in the following Table 1. The same operation was conducted with respect to seeds coated with the respective active ingredients individually, for comparison, as shown in Table 1. 7 days after the inoculation, the lesion area ratio on the first leaf was examined, and the control value was calculated based on the following formula. Further, theoretical values (control values) by use in combination were also calculated in accordance with the following Colby's formula.

Control value=$(1-a/b) \times 100$ a: lesion area ratio in treated plot
b: lesion area ratio in non-treated plot Colby's formula=$(X+Y+Z)-(XY+YZ+ZX)/100+XYZ/10{,}000$ X: control value of component (a) used singly
Y: control value of component (b) used singly
Z: control value of component (c) used singly

TABLE 1

| Compound/dose (g.a.i./100 kg seed) | Lesion area ratio (%) | Control value | Theoretical value |
|---|---|---|---|
| Pyriofenone 30 g | 50 | 44 | |
| Fluazinam 3.3 g | 90 | 0 | |
| 5 g | 90 | 0 | |
| 10 g | 90 | 0 | |
| Thiophanate-methyl 23.3 g | 90 | 0 | |
| 35 g | 60 | 33 | |
| 70 g | 50 | 44 | |
| Pyriofenone 30 g + fluazinam 3.3 g + thiophanate-methyl 23.3 g | 0 | 100 | 44 |
| Pyriofenone 30 g + fluazinam 5 g + thiophanate-methyl 35 g | 0 | 100 | 63 |
| Pyriofenone 30 g + fluazinam 10 g + thiophanate-methyl 70 g | 0 | 100 | 69 |

Lesion area ratio in non-treated plot: 90

INDUSTRIAL APPLICABILITY

According to the present invention, it is possible to provide a fungicidal composition having stable and high controlling effects against plant diseases, particularly preventive and/or curative effects against plant diseases.

The entire disclosure of Japanese Patent Application No. 2015-109896 filed on May 29, 2015 including specification, claims, drawings and summary is incorporated herein by reference in its entirety.

The invention claimed is:

1. A method for controlling plant diseases, comprising applying to plants, seeds and/or soil in which the plants or seeds grow a fungicidal composition comprising, as active ingredients, (a) pyriofenone, (b) fluazinam and (c) thiophanate-methyl, wherein application of (a), (b) and (c) together provides synergistic control of the plant diseases over (a), (b) or (c) applied alone.

2. The method for controlling plant diseases according to claim 1, wherein the plants are Gramineae crops, Leguminosae crops, Brassicaceae crops, Asteraceae crops, Solanaceae crops, Cucurbitaceae crops, Allioideae crops, Umbelliferae crops, Liliaceae crops, Polygonaceae crops, Convolvulaceae crops, Chenopodiaceae crops, Vitaceae crops, Rosaceae crops, Rutaceae crops, Ebenaceae crops, or Theaceae crops.

3. The method for controlling plant diseases according to claim 1, wherein the applying to plants, seeds and/or soil in which the plants or seeds grow comprises applying to seeds.

4. The method for controlling plant diseases according to claim 3, wherein in the applying to seeds, (a) pyriofenone, (b) fluazinam and (c) thiophanate-methyl are applied in a total amount of from 1 to 2,000 g/100 kg seed.

5. The method for controlling plant diseases according to claim 4, wherein the plants are Gramineae crops, Leguminosae crops, Brassicaceae crops, Asteraceae crops, Solanaceae crops, Cucurbitaceae crops, Allioideae crops, Umbelliferae crops, Liliaceae crops, Polygonaceae crops, Convolvulaceae crops, Chenopodiaceae crops, Vitaceae crops, Rosaceae crops, Rutaceae crops, Ebenaceae crops, or Theaceae crops.

6. The method for controlling plant diseases according to claim 2, wherein the weight ratio of two active ingredients selected from the group consisting of (a) pyriofenone, (b) fluazinam and (c) thiophanate-methyl is from 1:100 to 100:1.

7. The method for controlling plant diseases according to claim 6, wherein in the applying to seeds, (a) pyriofenone, (b) fluazinam and (c) thiophanate-methyl are applied in a total amount of from 1 to 2,000 g/100 kg seed.

8. The method for controlling plant diseases according to claim 2, wherein the applying to plants, seeds and/or soil in which the plants or seeds grow comprises applying to seeds.

9. The method for controlling plant diseases according to claim 2, wherein the weight ratio of two active ingredients selected from the group consisting of (a) pyriofenone, (b) fluazinam and (c) thiophanate-methyl is from 1:100 to 100:1.

10. The method for controlling plant diseases according to claim 8, wherein the weight ratio of two active ingredients selected from the group consisting of (a) pyriofenone, (b) fluazinam and (c) thiophanate-methyl is from 1:100 to 100:1.

11. The method for controlling plant diseases according to claim 5, wherein the weight ratio of two active ingredients selected from the group consisting of (a) pyriofenone, (b) fluazinam and (c) thiophanate-methyl is from 1:100 to 100:1.

12. A seed coated with a fungicidal composition comprising, as active ingredients, (a) pyriofenone, (b) fluazinam and (c) thiophanate-methyl, wherein combination of (a), (b) and (c) together provides synergy over (a), (b) or (c) alone.

13. The seed according to claim 12, which is coated with (a) pyriofenone, (b) fluazinam and (c) thiophanate-methyl in a total amount of from 1 to 2,000 g/100 kg seed.

14. The seed according to claim 12, which is a seed of Gramineae crops, Leguminosae crops, Brassicaceae crops, Asteraceae crops, Solanaceae crops, Cucurbitaceae crops, Allioideae crops, Umbelliferae crops, Liliaceae crops, Polygonaceae crops, Convolvulaceae crops, or Chenopodiaceae crops.

15. The seed according to claim 13, which is a seed of Gramineae crops, Leguminosae crops, Brassicaceae crops, Asteraceae crops, Solanaceae crops, Cucurbitaceae crops, Allioideae crops, Umbelliferae crops, Liliaceae crops, Polygonaceae crops, Convolvulaceae crops, or Chenopodiaceae crops.

16. The seed according to claim 12, wherein the weight ratio of two active ingredients selected from the group consisting of (a) pyriofenone, (b) fluazinam and (c) thiophanate-methyl is from 1:100 to 100:1.

17. The seed according to claim 13, wherein the weight ratio of two active ingredients selected from the group consisting of (a) pyriofenone, (b) fluazinam and (c) thiophanate-methyl is from 1:100 to 100:1.

18. The seed according to claim 14, wherein the weight ratio of two active ingredients selected from the group consisting of (a) pyriofenone, (b) fluazinam and (c) thiophanate-methyl is from 1:100 to 100:1.

19. The seed according to claim 15, wherein the weight ratio of two active ingredients selected from the group consisting of (a) pyriofenone, (b) fluazinam and (c) thiophanate-methyl is from 1:100 to 100:1.

* * * * *